(12) United States Patent
Bielstein et al.

(10) Patent No.: US 11,311,736 B2
(45) Date of Patent: Apr. 26, 2022

(54) SYSTEM FOR CONTROL OF MULTIPLE DEFIBRILLATION THERAPIES

(71) Applicant: Physio-Control, Inc., Redmond, WA (US)

(72) Inventors: Matthew L. Bielstein, Seattle, WA (US); Ryan W. Apperson, Bothell, WA (US); Reza Sharif, Lake Forest, WA (US); Kenneth P. Holmes, Monroe, WA (US); Wendy L. Warne, Seattle, WA (US)

(73) Assignee: Physio-Control, Inc., Redmond, WA (US)

( * ) Notice: Subject to any disclaimer, the term of this patent is extended or adjusted under 35 U.S.C. 154(b) by 69 days.

(21) Appl. No.: 16/920,153

(22) Filed: Jul. 2, 2020

(65) Prior Publication Data

US 2020/0360706 A1 Nov. 19, 2020

Related U.S. Application Data

(63) Continuation of application No. 15/788,671, filed on Oct. 19, 2017, now Pat. No. 10,702,701.

(60) Provisional application No. 62/410,283, filed on Oct. 19, 2016.

(51) Int. Cl.
| | |
|---|---|
| *A61N 1/39* | (2006.01) |
| *A61N 1/04* | (2006.01) |
| *A61N 1/36* | (2006.01) |
| *A61N 1/362* | (2006.01) |
| *A61N 1/06* | (2006.01) |
| *A61N 1/372* | (2006.01) |
| *A61N 1/375* | (2006.01) |

(52) U.S. Cl.
CPC ........... *A61N 1/3962* (2013.01); *A61N 1/046* (2013.01); *A61N 1/3622* (2013.01); *A61N 1/36146* (2013.01); *A61N 1/06* (2013.01); *A61N 1/3756* (2013.01); *A61N 1/37211* (2013.01)

(58) Field of Classification Search
None
See application file for complete search history.

(56) References Cited

U.S. PATENT DOCUMENTS

| | | | |
|---|---|---|---|
| 6,275,730 B1 | 8/2001 | KenKnight et al. | |
| 10,632,320 B1 * | 4/2020 | DeBardi | A61N 1/3937 |
| 2018/0280709 A1 * | 10/2018 | Taylor | A61N 1/3993 |

OTHER PUBLICATIONS

Erich, J., "Hold the Coroner," EMSWorld, published Apr. 30, 2011, retrieved from <<http://www.emsworld.com/article/10318805/hold-coroner>>, on Oct. 19, 2017, 3 pages.

(Continued)

*Primary Examiner* — Brian T Gedeon
(74) *Attorney, Agent, or Firm* — Lee & Hayes, P.C.

(57) ABSTRACT

A defibrillation system that includes a first defibrillation device and a second defibrillation device. The first defibrillation device including a therapy module, a communication module, a physiological parameter module and a timing control unit. The second defibrillation device including a therapy module and a communication module. The timing control unit configured to output an instruction to cause the therapy module of the first defibrillator and the therapy module of the second defibrillator to each discharge an energy delivery according to a timing relationship.

20 Claims, 4 Drawing Sheets

(56) References Cited

OTHER PUBLICATIONS

Johnson, et al., "Effect of Pulse Separation Between Two Sequential Biphasic Shocks Given Over Different Lead Configurations on Ventricular Defibrillation Efficacy," Circulation, American Heart Association, vol. 85, No. 6, Jun. 1992, pp. 2267-2274.

* cited by examiner

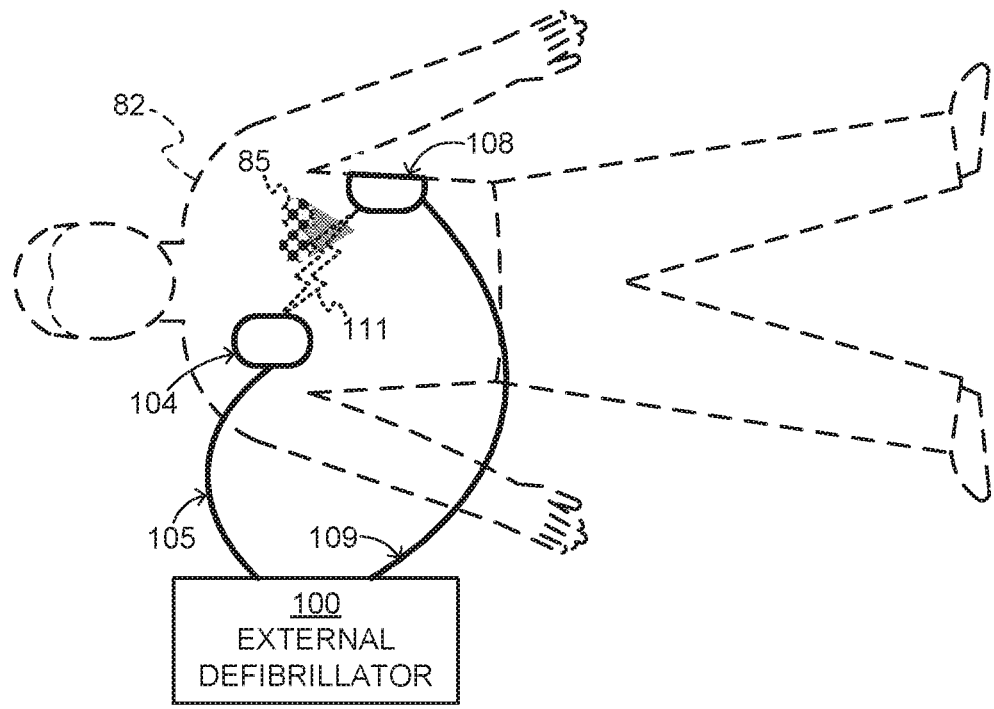
FIG. 1 *DEFIBRILLATION SCENE*
| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2 *TWO MAIN TYPES OF EXTERNAL DEFIBRILLATORS*

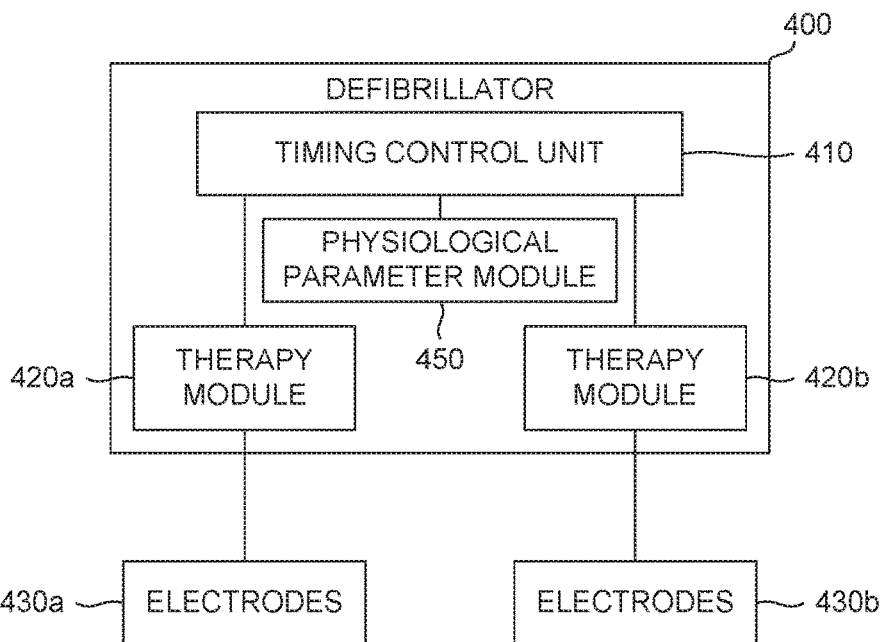
FIG. 4  *SINGLE DEFIBRILLATOR WITH MULTIPLE THERAPY MODULES*
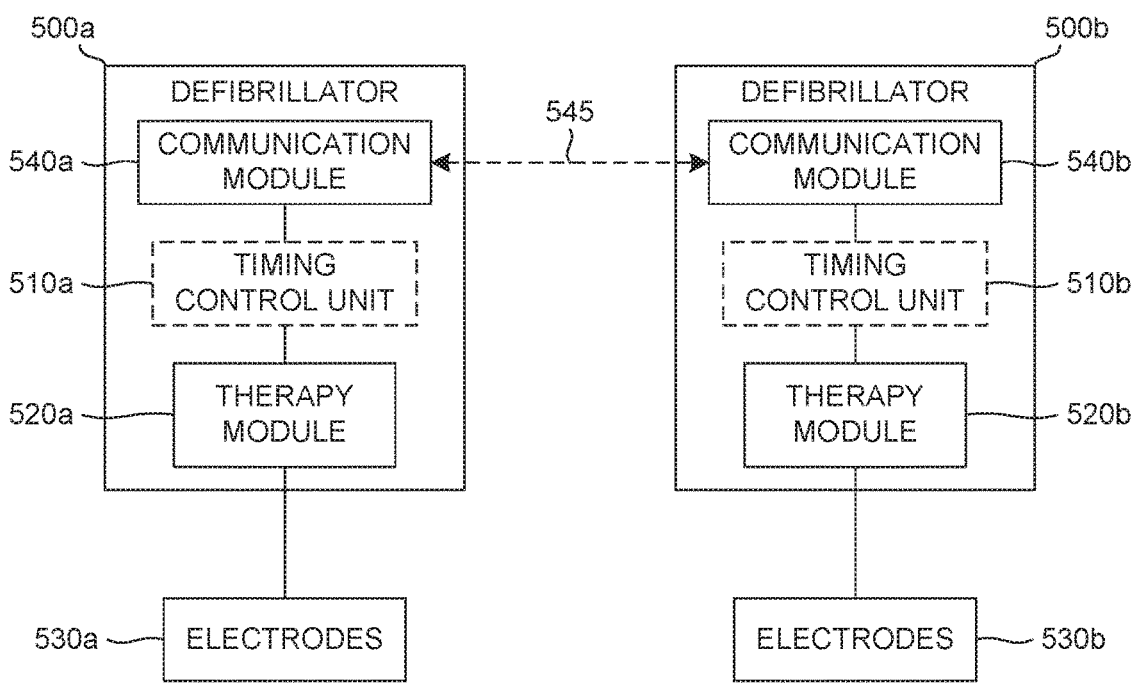
FIG. 5  *MULTIPLE DEFIBRILLATORS WITH SYNCHRONIZING MECHANISM*

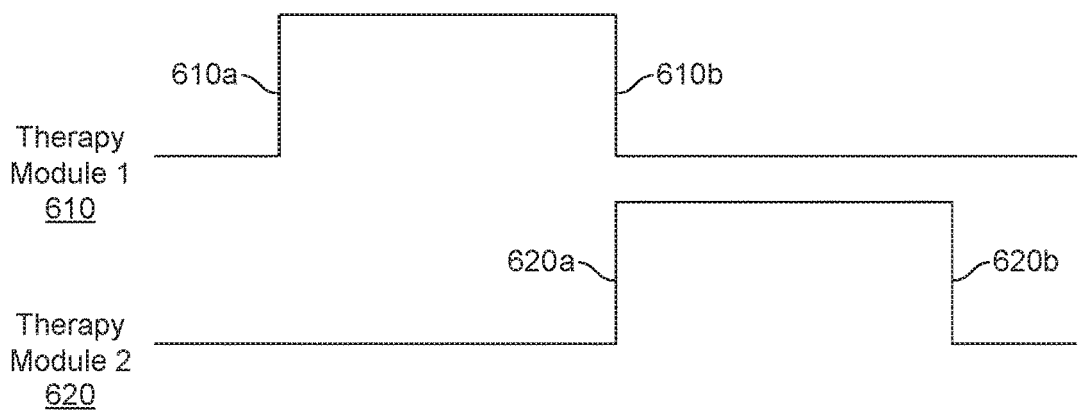
FIG. 6A  *EXAMPLE TIMING RELATIONSHIP*
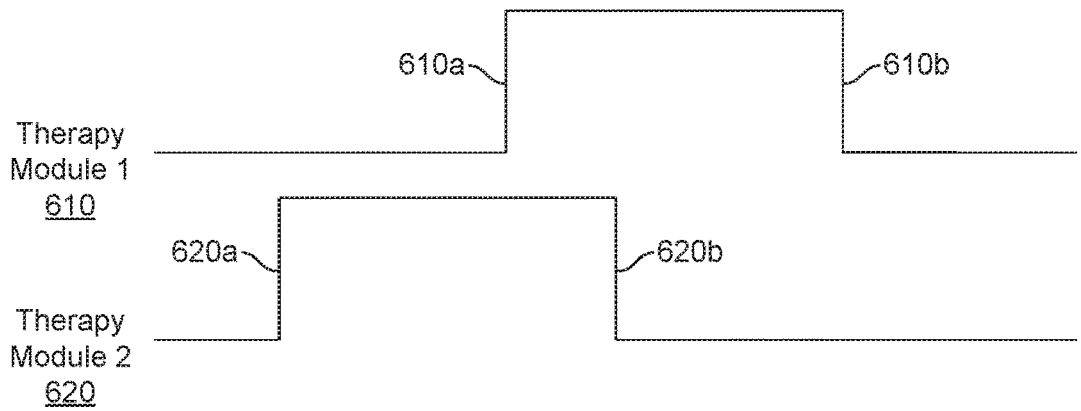
FIG. 6B  *EXAMPLE TIMING RELATIONSHIP*
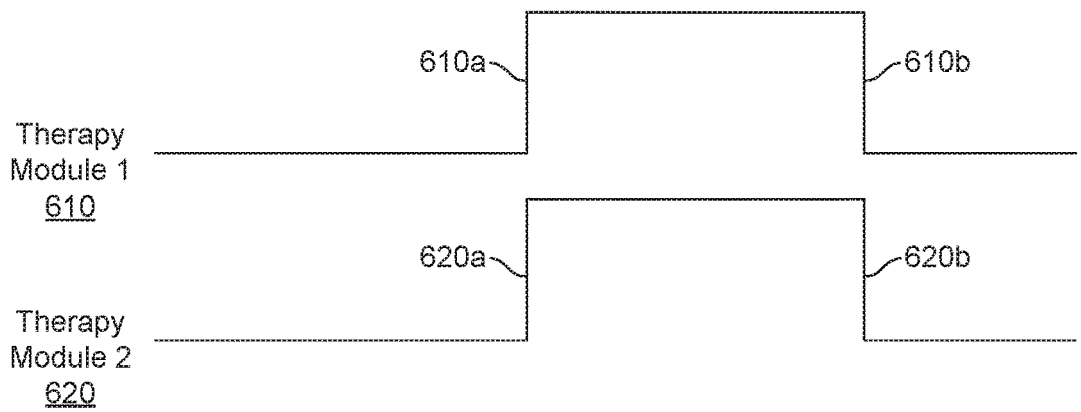
FIG. 6C  *EXAMPLE TIMING RELATIONSHIP*

SYSTEM FOR CONTROL OF MULTIPLE DEFIBRILLATION THERAPIES

CROSS-REFERENCE TO RELATED APPLICATIONS

This application is a continuation of U.S. patent application Ser. No. 15/788,671, filed on Oct. 19, 2017, which claims the benefit of U.S. Provisional Patent Application No. 62/410,283, filed on Oct. 19, 2016, the contents of each of which are herein incorporated by reference in their entirety.

BACKGROUND

Double sequential defibrillation (DSD), also sometimes referred to as simultaneous defibrillation is a recently developed treatment protocol that is growing in use and popularity to treat patients suffering from cardiac arrest. For a patient in ventricular fibrillation, and especially for a patient suffering from recurrent and uncontrolled ventricular fibrillation, the use of DSD or simultaneous defibrillation can be an effective treatment in restoring the patient's normal heart rhythm. DSD is considered by rescuers as a desperate last ditch effort to save the life of a cardiac arrest victim. Administration of DSD can be haphazard, poorly timed, and uncoordinated. DSD involves simultaneous defibrillation administered using two separate, same or distinct defibrillators, such as an automated external defibrillator (AED) and/or a standard defibrillator or monitor/defibrillator. Human rescuers have been observed to manually time the two (or more) defibrillation shocks to be delivered to the patient at the same time. Depending on the type of arrhythmia experienced by the patient, the timing of the shocks is different and the precision with which the shocks must be delivered for effective treatment is of great importance.

Relying on human ability and/or judgment to administer shocks from two separate defibrillators in a coordinated manner is an imperfect system that often resulted in ineffective therapy outcomes due to improper shock delivery timing. Improper timing of the shock delivery can also lengthen the time a patient experiences the cardiac event and treatment or can cause fatal additional arrhythmias to the patient's heart.

DSD and simultaneous defibrillation is becoming more widely adopted as a treatment for patients suffering from cardiac arrest. Presently, there is a need for a solution that would assist in properly delivering such therapies with precise timing control and reproducible timing of multiple shock, or energy deliveries. Further, new systems and/or methods for safe therapy administration is highly desirable.

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

FIG. 4 illustrates an example of a defibrillator with multiple therapy modules.

FIG. 5 illustrates an example of multiple defibrillators with a synchronizing mechanism.

FIGS. 6A-6C illustrate various examples of timing relationships for delivery of multiple defibrillation shocks.

SUMMARY

Figure 3:
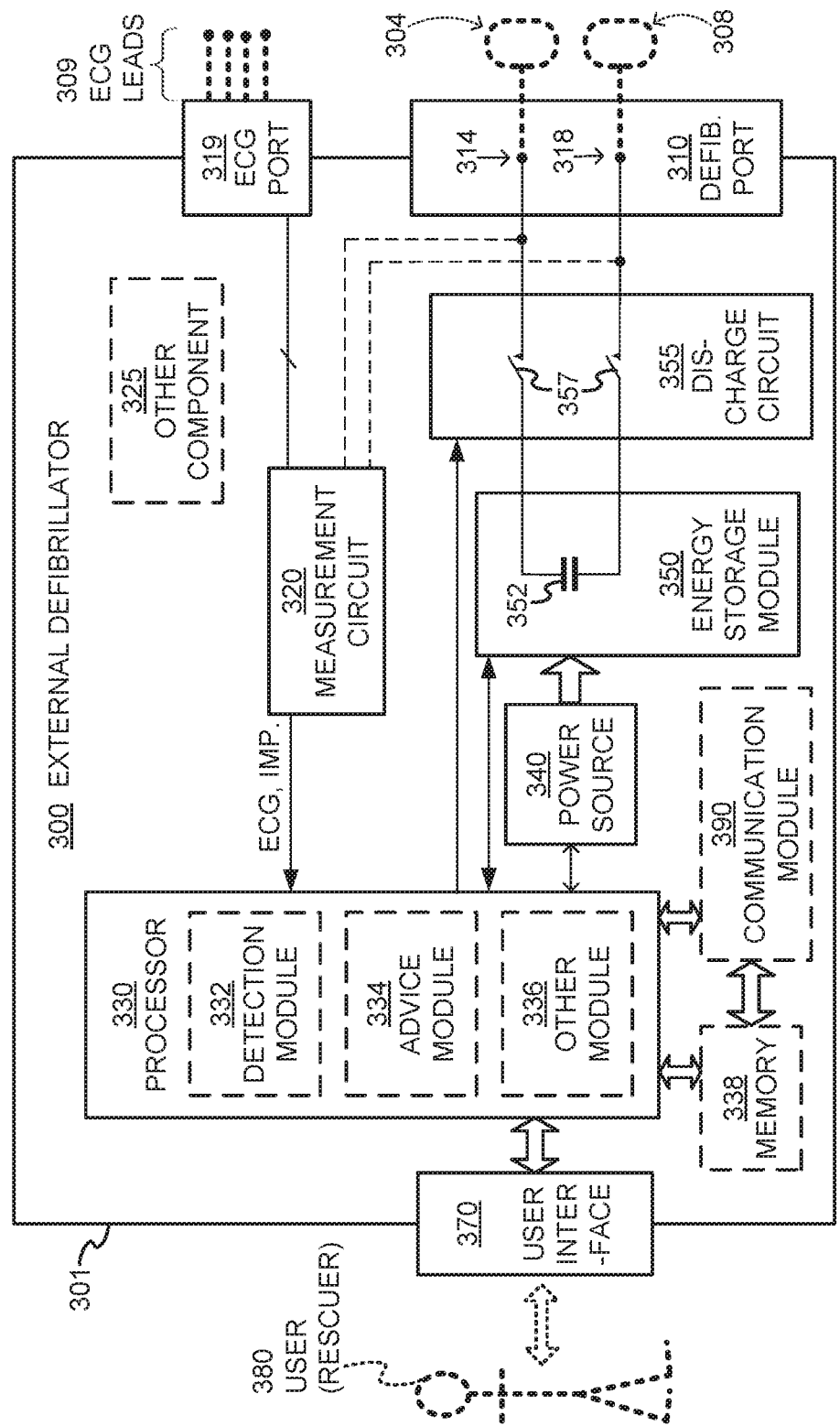
FIG. 3 is a functional block diagram showing components of an external defibrillator, such as the one shown in FIG. 1.

An example medical device can include a first therapy module, a second therapy module and timing control unit coupled to each. The timing control unit can receive patient data indicative of a shockable heart rhythm and determine at least two energy deliveries based on the received data. The two energy deliveries having a timing relationship relative to each other. The timing control unit generates instructions for the first therapy module to discharge a first energy and for the second therapy module to discharge a second energy according to the timing relationship.

In an example embodiment, a defibrillation device contains the first therapy module, the second therapy module and the timing control unit.

In a further example embodiment, the first energy delivery and the second energy delivery have a leading edge, a lagging edge and a duration. In an embodiment, the lagging edge of the first energy delivery can substantially coincide with the leading edge of the second energy delivery. In a further embodiment, the leading edge of the first energy delivery can substantially coincide with the leading edge of the second energy delivery.

In another example embodiment, the timing relationship can be determined automatically by one or more of the medical device of the timing control unit. In a further example embodiment, the timing relationship can be selected from one or more predetermined timing relationships.

In an example embodiment, one or more of the first energy delivery, the second energy delivery and the timing relationship can be based on one or more of the patient treatment data or at least one patient physiological parameter.

In a further example embodiment, the first therapy module and the timing control unit can be in a first medical device and the second therapy module can be in a second medical device. In another example embodiment, the first device can include a first communication module and the second medical device can include a second communication module, with the first communication module communicatively coupled to the second communication module via a communication link. In another example embodiment, the first communication module can be coupled to the timing control unit and configured to transmit the instruction to the second communication module, via the communication link, to cause the second energy delivery from the second therapy module. In a further example embodiment, the first medical device can automatically determine a proximity of the second medical device and establish a communication link between the first and second medical devices to communicatively couple the timing control unit of the first medical device and the second therapy module of the second device. In example embodiments, the communication link can use a polling protocol or a publish-subscribe protocol.

In an example embodiment, the timing control unit can include a processor and memory to store a series of instructions that when executed by the processor cause communication from the timing control unit to the first therapy module and the second therapy module in a predetermined manner. In another example embodiment, the timing control unit can include hardware that is configured to cause communication between the timing control unit and the first therapy module and the second therapy module in a predetermined manner.

In a further example embodiment, a first pair of electrodes can be coupled to the first therapy module and a second pair of electrodes can be coupled to the second therapy module. The first pair of electrodes can be configured to transmit at least a portion of the first energy delivery to a patient and the second pair of electrodes can be configured to transmit at least a portion of the second energy delivery to the patient.

An example patient defibrillation system can include a first defibrillation device and second defibrillation device. The first defibrillation device can include a first therapy module configured to output a first energy delivery having a first leading edge, a first lagging edge and a first duration. The first defibrillation device can also include a first communication module and physiological parameter module that is configured to cause a physiological output based on one or more physiological parameters of a patient. A timing control unit can also be included in the first defibrillation device and can be coupled to the first therapy module, the first communication module and the physiological parameter module. The timing control unit can be configured to output an instruction in response to the physiological output and the instruction, based on a timing relationship, can cause output of the first energy delivery by the first therapy module and can cause at least a portion of the instruction to be transmitted by the first communication module. The second defibrillation device can include a second therapy module configured to output a second energy delivery having a second leading edge, a second lagging edge and a second duration. The second defibrillation device can also include a second communication module that is communicatively coupled to the first communication module of the first defibrillation device and to the second therapy module. The second communication module can receive at least a portion of the instruction causing output of the second energy delivery by the second energy delivery module, such that one or more of the second leading edge, the second lagging edge and the second duration occurs relative to one or more of the first leading edge, the first lagging edge and the first duration based on the timing relationship.

In an example embodiment, one or more of the first leading edge, the first lagging edge and the first duration of first energy delivery and one or more of the second leading edge, the second lagging edge and the second duration can be based on the one or more physiological parameters of the patient.

In a further example embodiment, the at least a portion of the instruction can include at least one of the second leading edge, the second lagging edge and the second duration of the second energy delivery relative to the one or more of the first leading edge, the first lagging edge and the first duration.

DETAILED DESCRIPTION

Described herein are methods and systems for controlling multiple defibrillation therapies, such as dual sequential defibrillation (DSD) and simultaneous defibrillation. DSD is the administration of multiple defibrillation therapies, or energy deliveries, the administration of each timed relative to one or more preceding administration. Simultaneous defibrillation is the administration of multiple defibrillations, or energy deliveries, substantially concurrently. The administration of multiple defibrillations and/or energy therapies has been used to assist with correcting an abnormal heart rhythm of patient cardiac event victim. The systems and methods described below provide a controlled, adjustable and repeatable means for delivery of such defibrillation therapies so as to assist in the correction of an abnormal heart rhythm. FIGS. 1-3 explain a general overview of defibrillation therapy using a single defibrillation or therapy module for sake of simplifying the general explanation. FIGS. 4-6C relate specifically to DSD and/or simultaneous defibrillation using two or more therapy modules and/or defibrillators.

FIG. 1 is a diagram of a defibrillation scene in which a patient is receiving defibrillation therapy from a single external defibrillator 100. The person 82 is lying on his or her back and could be a patient in a hospital, or someone found unconscious, and then turned to be on their back. The person 82 is experiencing a cardiac arrhythmia in his or her heart 85, which could be Ventricular Fibrillation (VF) for example.

A portable external defibrillator 100 has been brought close to the person 82. At least two defibrillation electrodes 104, 108 are usually provided with an external defibrillator 100, and are sometimes called electrodes 104, 108. The electrodes 104, 108 are coupled with the external defibrillator 100 via respective electrode leads 105, 109. A rescuer (not shown) has attached electrodes 104, 108 to the skin of person 82 and actuates the defibrillator 100 to administer a brief, strong electric pulse 111 via electrodes 104, 108 through the body of person 82. Pulse 111, also known as a defibrillation shock, goes also through heart 85, in an attempt to restart it by depolarizing the cardiac cells and resetting the natural pace for the heart, for saving the life of the person 82.

The defibrillator 100 can be one of different types, each with different sets of features and capabilities. The set of capabilities of the defibrillator 100 is determined by planning who would use it, and the training those rescuers would be likely to have. Examples are now described.

FIG. 2 is a table listing two main types of external defibrillators, and their primary users. A first type of defibrillator 100 is generally called a defibrillator-monitor because it is typically formed as a single defibrillation unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. and often requires technical training on its operation. Such a defibrillator-monitor is intended to be used in a pre-hospital or hospital scenario.

As a defibrillator, the device can be one of different varieties, or even versatile enough to be able to switch among different modes that individually correspond to the device varieties. One variety is that of an automated defibrillator, which can determine whether a shock is needed and, if so, charge a therapy module of the device to a predetermined energy level and instruct and/or prompt the user to administer the shock. Another variety is that of a manual defibrillator where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signal or impedance between two electrodes. Additionally, these signals can relate to the person's temperature, non-invasive blood pressure (NIBP), arterial oxygen saturation/pulse oximetry (SpO2), the concentration or partial pressure of carbon dioxide in the respiratory gases, known as capnography, and so on. These signals can be further stored and/or transmitted as patient data.

A second type of external defibrillator 100 is generally called an AED, which stands for "Automated External Defibrillator". An AED typically automatically makes the shock/no shock determination on whether to deliver defibrillation therapy to the patient. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, hospitals, for example, may deploy AEDs at its various floors, in case the more expensive defibrillator-monitor is more critically being deployed at an Intensive Care Unit or other emergency situation of greater need, and so on.

AEDs, however, can also be used by people who are not in the medical profession. More particularly, an AED can be used by many professional first responders, such as the police, firefighters, emergency medical personnel, etc. AEDs are often found in public locations especially those locations that tend to host large numbers of people. Such AEDs are often operated by rescuers with first-aid training or by a good Samaritan who has no training on the device at all AEDs increasingly can supply instructions to whoever is using them and anticipate this wide variety of skill levels of its users.

AEDs are thus particularly useful because clinical response time is very critical when responding to someone suffering VF. Indeed, the people who are able to first reach the VF sufferer may not be and are often not in the medical professions.

There are additional types of external defibrillators that are not listed in FIG. 2. For example, a hybrid defibrillator can have aspects of an AED and also of a defibrillator-monitor. A usual such aspect is additional ECG monitoring capability among others.

FIG. 3 is a diagram showing components of an external defibrillator 300 made according to embodiments. These components can be, for example, in the external defibrillator 100 of FIG. 1. Additionally, the components of FIG. 3 can be provided in a housing 301, which can also be known as a casing 301. The external defibrillator 300 is intended for use by a user 380, who is the rescuer. The defibrillator 300 typically includes a defibrillation port 310, such as a socket in the housing 301. The defibrillation port 310 includes nodes 314, 318. The defibrillation electrodes 304, 308, which can be similar to the electrodes 104, 108, can be connected to the defibrillation port 310 so as to make an electrical connection with the nodes 314, 318, respectively. It is also possible that electrodes can be connected continuously to the defibrillation port 310, etc. Either way, the defibrillation port 310 can be used for guiding an electrical charge that has been stored in the defibrillator 300 to the person 82 through the electrodes.

If the defibrillator 300 is a defibrillator-monitor, as was described with reference to an example discussed in FIG. 2, then it will typically also have an ECG port 319 in housing 301, for plugging in ECG leads 309. ECG leads 309 can help sense an ECG signal, e.g. a 12-lead signal, or from a different number of leads. Moreover, a defibrillator-monitor could have additional ports (not shown), and another component 325 structured to filter the ECG signal, e.g., apply at least one filter to the signal so as to remove chest compression artifacts resulting from chest compressions being delivered to the person 82. The defibrillator 300 shown in FIG. 3 also includes a measurement circuit 320 that receives patient physiological signal(s) from the ECG port 319, and also from other ports, if provided. These physiological signals are sensed, and information about them is rendered by the circuit 320 as data, or other signals, etc.

If the defibrillator 300 is an AED, it may lack an ECG port 319. The measurement circuit 320 can obtain physiological signals through nodes 314, 318 instead, when defibrillation electrodes 304, 308 are attached to person 82. In these examples, a patient's ECG signal can be sensed as a voltage difference between the electrodes 304, 308. Further, impedance values sensed between the electrodes 304, 308 can be detect, among other things, whether these electrodes 304, 308 have been inadvertently disconnected from the person.

The defibrillator 300 also includes a processor 330 that may be implemented in any number of ways. Such ways include, by way of example and not limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 330 can be include a number of modules. One such module is a detection module 332, which senses outputs of measurement circuit 320. Detection module 332 can include a VF detector. Thus, the person's sensed ECG can be used to determine whether the person is experiencing VF. Another such module in the processor 330 is an advice module 334, which arrives at advice based on output(s) of the detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report the shock recommendation to the user, and prompt them to do it. Other embodiments further execute the advice, by administering the shock. If the advice is to administer CPR, the defibrillator 300 may further issue prompts for it, and so on. The processor 330 can include additional modules, such as the module 336, for other functions. In addition, if another component 325 is indeed provided, it may be operated in part by the processor 330, etc.

Defibrillator 300 optionally further includes a memory 338, which can work together with the processor 330. The memory 338 may be implemented in any number of ways. Such ways include, by way of example and not of limitation, nonvolatile memories (NVM), read-only memories (ROM), random access memories (RAM), any combination of these, and so on. The memory 338, if provided, can include programs for the processor 330, and so on. The programs can be operational for the inherent needs of the processor 330, and can also include protocols and ways that decisions can be made by the advice module 334. In addition, the memory 338 can store prompts for the user 380 and patient data, as needed.

The defibrillator 300 may also include a power source 340. To enable portability of the defibrillator 300, the power source 340 typically includes a battery. Such a battery can be implemented as a battery pack, which may be rechargeable or not. Sometimes, a combination is used, of rechargeable and non-rechargeable battery packs. Other embodiments of power source 340 can include AC power override that allows a rescuer to use AC power when such a source exists, but rely on the battery power if AC power is unavailable. In some embodiments, the power source 340 is controlled by the processor 330. The defibrillator 300 additionally includes an energy storage module 350. The module 350 is where some electrical energy is stored, when preparing the device for sudden discharge to administer defibrillation shock therapy to the patient. The module 350 can be charged from the power source 340 to the desired amount of energy, as controlled by the processor 330. In typical implementations, the module 350 includes one or more capacitors 352 that charge and help store the energy for later discharge, and so on.

The defibrillator 300 can also include a discharge circuit 355. The discharge circuit 355 can be controlled to permit the energy stored in the module 350 for discharge to the nodes 314, 318, and thus also to the defibrillation electrodes 304, 308. The discharge circuit 355 can include one or more switches 357. Those switches can be made in a number of ways, such as by an H-bridge, and so on, or other desirable configurations.

The defibrillator 300 further includes a user interface 370 for the user 380. For example, the interface 370 may include a screen to display what is detected and measured, provide visual feedback to the rescuer for their resuscitation attempts, and so on. The interface 370 may also include a speaker to issue voice prompts or otherwise audibly interact with the user and may additionally include various controls, such as pushbuttons, keyboards, and so on, as needed or desired. In addition, the discharge circuit 355 can be controlled by the processor 330, or directly by the user 380 through the user interface 370.

The defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and the like. Another feature of a defibrillator can be CPR-prompting in which prompts are issued to the user, visual or by sound or otherwise, so that the user can administer CPR and/or receive feedback/instructions regarding the administration of CPR and/or delivery of shock therapy to the patient.

FIG. 4 shows an example defibrillator 400 capable of delivering DSD and/or simultaneous defibrillation therapy to a patient. The defibrillator 400 includes a timing control unit 410, a physiological parameter module 450 and two therapy modules 420a, 420b that are connected to respective electrodes 430a, 430b. Any suitable number of therapy modules and respective electrodes could be used in alternative configurations. In this example, the defibrillator has a single housing that includes each of the timing control unit 410, the physiological parameter module 450, and the two therapy modules 420a, 420b, e.g., the defibrillator 400 is a single medical device. The defibrillator 400 can be connected to a patient through the electrodes 430a, 430b and can receive various patient data relevant to applying a custom treatment protocol, such as patient physiological data, to monitor the patient and to determine the presence of a shockable heart rhythm. In response to a shockable heart rhythm and/or an instruction to deliver a shock, the therapy modules 420a, 420b, when triggered via instructions from the timing control unit 410, can deliver an energy discharge to a patient through electrodes 430a, 430b. The energy discharge is a defibrillation shock or shock therapy that helps reset the heart's normal electrical activity.

Patient physiological or treatment data can be received by the patient physiological module, if one is present. 450 of the defibrillator 400 from one or more sensors and/or systems, such as a patient monitor. Electrocardiogram (ECG) data can be included in the patient physiological data to provide data regarding the functioning of a patient's heart, such as a heart rhythm. The patient physiological module 450, or other system, can analyze the received patient physiological data to determine if an energy delivery to the patient is appropriate and/or necessary. In response to determining that such an energy delivery should occur, the physiological parameter module 450 can cause the timing control unit 410 to generate and/or transmit instructions to the therapy modules 420a, 420b to deliver energy to the patient based on a selected and/or calculated timing relationship between the two therapy modules 420a, 420b.

The timing control unit 410 is electrically connected to each of the therapy modules 420a, 420b and generates instructions to control the energy discharge and/or delivery of shock therapy from one or both of the therapy modules 420a, 420b. Based on the patient treatment data received by the defibrillator 400, the timing control unit 410 can generate instructions for the therapy modules 420a, 420b to coordinate the energy delivery from each module with respect to each other's therapy delivery. The instructions can include various characteristics of the energy delivery from each of the therapy modules 420a, 420b, such as the timing of the energy delivery, an amount of energy to deliver and/or other energy delivery characteristics.

The timing of the energy delivery from each of the therapy modules 420a, 420b can be coordinated such that the total energy delivery from the therapy modules 420a, 420b is delivered as desired, or required, such as to deliver an effective defibrillation shock therapy to a patient's heart. The timing unit 410 instructions can cause the energy delivery from each of the therapy modules 420a, 420b to be precisely delivered such that each delivery substantially overlaps each other, partially overlaps or does not overlap at all. The coordinated energy delivery from the therapy modules 420a, 420b can result in a more effective treatment of a shockable heart rhythm of a patient.

As mentioned above, the timing control unit 410 can transmit instructions to the therapy modules 420a, 420b to cause energy delivery from each of the therapy modules 420a, 420b. The transmission of the instructions can be effected by a software messaging mechanism, digital trigger and/or other triggering means to cause the energy delivery from the therapy modules 420a, 420b in a coordinated manner. In a further embodiment, each of the therapy modules 420a, 420b can be connected to a separate timing control unit. One or more of the timing control units can communicate with, or otherwise provide information to, the other timing control units to cause the coordinated energy delivery from each of the therapy modules 420a, 420b, as based on the timing relationship.

Each therapy module 420a, 420b, and/or the defibrillator 400, can include an isolation relay, or relays, to isolate one or more of the defibrillator 400, and/or therapy modules 420, 420b, from feedback caused by an energy delivery. The isolation relay can prevent feedback from an energy delivery of a therapy module into one or more other therapy modules.

The defibrillator 400, as shown in FIG. 4, is a single unit with two therapy modules 420a, 420b housed within. While shown as two separate elements, the therapy modules 420a, 420b can also be submodules/subdivisions of a single therapy module. Alternatively, the two therapy modules 420a, 420b can be separated and integrated into a single therapy module. In a further embodiment, the defibrillator 400 can include a single therapy module capable of multiple, coordinated energy deliveries.

The electrodes 430a, 430b are similarly shown as separate elements in FIG. 4; however, the therapy modules 420a, 420b can be connected to a single electrode pair for energy delivery to a patient. In an embodiment, the defibrillator 400 can include connections to associate an electrode pair with each of the therapy modules, as shown in FIG. 4, and a connection that allows a single pair of electrodes to facilitate energy delivery from each therapy module of the defibrillator.

Alternatively, the timing relationship between the energy delivery by each of the therapy modules 420a, 420b can be based on sensing an energy delivery by one or more of the therapy modules 420a, 420b. For example, a first therapy module 420a can output a first energy delivery, the first energy delivery can be detected by a second therapy module 420b through second electrodes 430b. Sensing the first energy delivery, the second therapy module 420b can output a second energy delivery based on the sensed first energy delivery, in a predetermined manner and/or other timing relationship.

FIG. 5 illustrates an example pair of separate and distinct defibrillators 500a, 500b that capable of a coordinated energy delivery of multiple defibrillation shock therapy based on a precise timing relationship. In the example shown, two defibrillators 500a, 500b communicate with each other to coordinate energy delivery from each of their respective therapy modules 520a, 520b based on a timing relationship. Each of the defibrillators 500a, 500b include a communication module 540a, 540b and a therapy module 520a, 520b, connected to electrodes 530a, 530b. One or more of the defibrillators 500a, 500b also includes a timing control unit 510a, 510b that coordinates the energy delivery from each of the therapy modules 520a, 520b of the defibrillators 500a, 500b.

The communication module 540a, 540b of each defibrillator 500a, 500b, communicates with their respective counterpart through a connection 545 that can be a wired and/or wireless connection. The wireless connection can include a direct wireless connection between the defibrillators 500a, 500b, and/or a wireless connection through a larger network. Further, the combination between the defibrillators 500a, 500b can use a combination of wired and wireless connections and/or networks. Example wireless connection can include infrared, radio, Bluetooth®, Wi-Fi and/or other communication networks. The communication modules 540a, 540b can also be configured to communicate any data to a larger computing platform, such as a comprehensive network of connected points-of-care along a treatment pathway or among multiple connected treatment pathways. The communication modules 540a, 540b can also connect to remote locations as well, such as a hospital or advice center to aid the care team both at the instant point-of-care and at the next point-of-care along the treatment pathway.

Data, such as patient physiological data and/or a timing relationship, can be communicated from one defibrillator 500a, 500b to another defibrillator 500a, 500b via the connection 545. For a timing relationship, the data exchanged and/or transmitted can include a clock signal to synchronize the defibrillators 500a, 500b, a trigger to cause one or more of the defibrillators 500a, 500b to deliver energy to the patient, a timed delay for delivery of energy from the receiving defibrillator 500a, 500b and/or other timing relationship information necessary to coordinate the delivery of energy from the defibrillators 500a, 500b based on a timing relationship.

Various communication protocols and/or styles can be used to effect communication between the two or more defibrillators 500a, 500b. Example communications can include polling and/or publish-subscribe. In a polling arrangement, one of the defibrillators 500a, 500b acts as a master and the remaining defibrillators are slaves. The master defibrillator broadcasts the message, or data, to all of the slave defibrillators and can then poll each defibrillator in turn to receive a response and/or other information. In a publish-subscribe arrangement each defibrillator can publish a message, or data, that is tagged with one or more categories and subscriber defibrillators receive and process the message if the category of the published message, or data, matches one they are monitoring. Alternatively, the defibrillators 500a, 500b can use other messaging and/or data transmission protocols to exchange information and/or data, such as a timing relationship.

In an example embodiment, both defibrillators 500a, 500b can include a timing control unit 510a, 510b that transmits instructions for energy delivery to the respective therapy module 520a, 520b coupled thereto. In this arrangement, one of the defibrillators 500a, 500b can act as a primary defibrillator that transmit instructions to the other one or more defibrillators 500a, 500b to cause the delivery of energy to the patient based on a timing relationship. The primary defibrillator can transmit the selected and/or calculated timing relationship, or data, to the other, secondary, defibrillator via the connection 545. Additionally, the timing relationship can include a clock or other signal to synchronize the various timing elements of each of the defibrillators 500a, 500b. In response to the received timing relationship, the communication module 540a, 540b and/or the timing control unit 510a, 510b, of the secondary defibrillator can transmit instructions to and/or cause the therapy module 520a, 520b of the secondary defibrillator to deliver energy to the patient based on the timing relationship.

In an alternative embodiment, the secondary defibrillator 500a, 500b can be a secondary device that can communicate with the primary defibrillator 500a, 500b and deliver energy to a patient when triggered and/or instructed to do so. In this manner, the secondary device can be a "dumb" device that is only capable of energy delivery when triggered, and cannot perform patient physiological data acquisition and/or analysis. The "dumb" nature of the secondary device can reduce the required complexity and/or cost of the secondary device needed to cause the synchronized delivery of multiple energies.

In an example, a "dumb" device could include older model defibrillators that lack one or more abilities of newer and/or more current defibrillators. The older defibrillators can be modified and/or equipped with a communication module, or means, allowing them to be used for the coordinated delivery of energy to the patient as described herein.

FIGS. 6A-6C illustrate example timing relationships for delivery of energy from one or more therapy modules 610, 620 of one or more devices, such as a defibrillator of FIG. 4 or the multiple defibrillators of FIG. 5. Each energy delivery has a leading edge, or beginning/initiation, of an energy delivery and a lagging edge, or ending/termination, of the energy delivery. The various timing relationships can be based on the relative timing between the various leading and/or lagging edges of the one or more energy deliveries. Patients suffering from some cardiac arrhythmias, specifically persistent VF, for example, respond well to either or both of an increase in the time duration and/or the magnitude of the energy delivery.

In the example of FIG. 6A, a first energy delivery from a first therapy module 610 has a leading edge 610a, a lagging edge 610b and a first duration that spans between the edges of the first energy delivery. A second energy delivery from a second therapy module 620 has a leading edge 620a, a lagging edge 620b and a second duration that spans between the edges of the second energy delivery. While the magnitudes and/or durations of the various first and second energy deliveries shown in FIGS. 6A-6C are shown as substantially the same, the magnitude and/or duration of the first and second energy deliveries can be substantially the same or different, based on the patient physiological/treatment data and/or as required/desired. DSD therapy has been shown to be effective for correcting cardiac arrhythmias by one or both of lengthening the amount of time the shock therapy is being delivered to the patient and/or by increasing the magnitude of energy delivered to the patient.

In the example timing relationship shown in FIG. 6A, the second energy delivery from the second therapy module 620 is timed so that the leading edge 620a of the second energy delivery substantially coincides or immediately precedes the lagging edge 610b of the first energy delivery. This timing arrangement causes the first and second energy deliveries to be substantially continuous or occur closely spaced apart. Further, while the first energy delivery by the first therapy module 610 is shown as occurring prior to the second energy delivery by the second therapy module 620, the occurrence and/or timing of the first and second energy deliveries can be switched, with the leading edge 610a of the first energy delivery being closely spaced to or occurring substantially simultaneously as the lagging edge 620b of the second energy delivery. The back-to-back delivery of the shock therapies lengthens the time duration of the delivery to the patient's heart and may help reset it natural rhythm.

In the example of FIG. 6B, the first and second energy deliveries are shown as overlapping. The leading edge 610a of the first energy delivery of the first therapy module 610 is shown as occurring prior to the lagging edge 620b of the second energy delivery of the second therapy module 620. Such overlap between the two energy deliveries causes a peak of shock during the time duration of the overlap with shock before and after either being approximately equal in magnitude or varying, depending on the configuration and therapy protocol. Delivery of energy in such a manner can be advantageous if the leading and/or lagging edges of one or more of the energy deliveries has slope to, or from, the ultimate magnitude of the energy delivery. The overlapping delivery of the shock therapies lengthens the overall time that the patient receives the shock therapy and creates a peak magnitude of an increase of energy in the middle of the delivery of the two shock therapies.

In the example of FIG. 6C, the first and second energy deliveries are shown as occurring substantially simultaneously. The leading edge 610a of the first energy delivery by the first therapy module 610 substantially coincides, or occurs with, the leading edge 620a of the second energy delivery by the second therapy module 620. In the example shown, the lagging edges 610, 620b of the first and second energies are also shown as substantially coinciding as the first and second energies have substantially the same duration. In other embodiments, the duration of the first and second energy deliveries can be different such that the lagging edges 610b, 620b of the energy deliveries do not coincide. Alternatively, the leading edges 610a, 620a of the energy deliveries may occur at different times and the lagging edges 610b, 620b of the energy deliveries can be coincident. The simultaneous or near simultaneous delivery of the two shock therapies increases the magnitude of energy delivered to the patient but does not lengthen or substantially change the length of the duration of the shock therapy delivery.

The timing of the delivery of both of the energy deliveries shown in each of the timing relationship configurations shown in FIGS. 6A-6C can be timed precisely with various segments of a patient's ECG signal, if the ECG signal is being sensed during the shock therapy. Specifically, the timing relationship may increase the duration and/or the magnitude of the energy deliveries in persistent VF for example and can be customized to other cardiac arrhythmias as needed.

The timing control unit of one or more defibrillators can use a timing relationship, such as those described above, to coordinate the delivery of multiple shocks and/or energies to a patient. Various characteristics of the energy delivery, such as a leading edge, lagging edge and/or duration, can be used to time the energy deliveries relative to each other of a synchronized clock or timing. Further, while the examples above are shown with two therapy modules, defibrillators and/or devices, additional therapy modules, defibrillators and/or device can be used to deliver multiple energies to a patient in a coordinated manner based on one or more timing relationships between the energy deliveries.

It will be appreciated that variants of the above-disclosed and other features and functions, or alternatives thereof, may be combined into many other different systems or applications. Other embodiments Various presently unforeseen or unanticipated alternatives, modifications, variations, or improvements therein may be subsequently made by those skilled in the art which are also intended to be encompassed by the following claims.

The invention claimed is:

1. A defibrillation system, comprising:
   a first external defibrillator, comprising:
      a physiological parameter module configured to receive electrocardiogram (ECG) data of a patient and to determine, based on the ECG data, that a heart of the patient is exhibiting a shockable rhythm;
      a timing control unit configured to determine, based on the ECG data, a timing relationship between a first defibrillation shock and a second defibrillation shock;
      a first communication module configured to transmit an instruction indicating the timing relationship; and
      a first therapy module configured to output the first defibrillation shock to the patient; and
   a second external defibrillator, comprising:
      a second communication module configured to receive the instruction from the first external defibrillator; and
      a second therapy module configured to output, based on the timing relationship, a leading edge of the second defibrillation shock to the patient at a different time than a lagging edge of the first defibrillation shock.

2. The defibrillation system of claim 1, wherein the different time is subsequent to the lagging edge of the first defibrillation shock.

3. The defibrillation system of claim 1, wherein the different time is prior to the lagging edge of the first defibrillation shock.

4. The defibrillation system of claim 1, wherein the first external defibrillator further comprises:

first electrodes coupled to skin of the patient; and
a first discharge circuit configured to output the first defibrillation shock to the first electrodes, and
wherein the second external defibrillator further comprises:
second electrodes coupled to the skin of the patient; and
a second discharge circuit configured to output the second defibrillation shock to the second electrodes.

5. The defibrillation system of claim 1, wherein each of a first magnitude of the first defibrillation shock and a second magnitude of the second defibrillation shock is smaller than a combined magnitude of the first defibrillation shock and the second defibrillation shock occurring prior to a lagging edge of the second defibrillation shock and after a leading edge of the first defibrillation shock.

6. A primary defibrillator, comprising:
a timing control unit configured to determine a timing relationship between a first defibrillation shock and a second defibrillation shock;
a communication module configured to transmit an instruction to a secondary defibrillator, the instruction indicating the timing relationship and causing the secondary defibrillator to output the second defibrillation shock based on the timing relationship; and
a therapy module configured to output the first defibrillation shock, a lagging edge of the first defibrillation shock being at a different time than a leading edge of the second defibrillation shock.

7. The primary defibrillator of claim 6, wherein the instruction causes the secondary defibrillator to output the second defibrillation shock subsequent to the lagging edge of the first defibrillation shock.

8. The primary defibrillator of claim 6,
wherein each of a first magnitude of the first defibrillation shock and a second magnitude of the second defibrillation shock is smaller than a combined magnitude of the first defibrillation shock and the second defibrillation shock occurring after the leading edge of the second defibrillation shock and prior to the lagging edge of the first defibrillation shock.

9. The primary defibrillator of claim 6, wherein the therapy module comprises a discharge circuit configured to output the first defibrillation shock to electrodes that are coupled to a patient.

10. The primary defibrillator of claim 6, wherein the communication module is configured to transmit the instruction over a wired or a wireless connection with the secondary defibrillator.

11. The primary defibrillator of claim 6, further comprising:
a measurement circuit configured to receive an electrocardiogram (ECG) signal of a patient and to identify a shockable rhythm based on the ECG signal,
wherein the timing control unit is configured to determine the timing relationship based on the shockable rhythm.

12. The primary defibrillator of claim 11, wherein the shockable rhythm comprises persistent ventricular fibrillation (VF).

13. The primary defibrillator of claim 6, wherein each of a first magnitude of the first defibrillation shock and a second magnitude of the second defibrillation shock is smaller than a combined magnitude of the first defibrillation shock and the second defibrillation shock occurring prior to a lagging edge of the second defibrillation shock and after a leading edge of the first defibrillation shock.

14. A method, comprising:
determining, based at least in part on physiological data of a patient, that a heart of the patient is exhibiting a shockable rhythm;
determining a timing relationship between a first defibrillation shock and a second defibrillation shock based, at least in part, on the physiological data;
causing a first therapy module of a first defibrillator to discharge the first defibrillation shock to the patient in accordance with the timing relationship; and
causing a second therapy module of a second defibrillator to discharge the second defibrillation shock to the patient in accordance with the timing relationship, a leading edge of the second defibrillation shock being at a different time than a lagging edge of the first defibrillation shock.

15. The method of claim 14, wherein the physiological data comprises an electrocardiogram (ECG) measurement, a blood pressure measurement, a pulse oximetry measurement, or a capnography measurement.

16. The method of claim 14, wherein the different time is subsequent to the lagging edge of the first defibrillation shock.

17. The method of claim 14, wherein the different time is prior to the lagging edge of the first defibrillation shock.

18. The method of claim 17, wherein causing the first therapy module to discharge the first defibrillation shock in accordance with the timing relationship comprises causing the first therapy module to discharge the first defibrillation shock to the patient,
wherein causing the second therapy module to discharge the second defibrillation shock in accordance with the timing relationship comprises causing the second therapy module to discharge the second defibrillation shock to the patient, and
wherein a peak energy delivered to the patient occurs after the leading edge of the second defibrillation shock and before the lagging edge of the first defibrillation shock.

19. The method of claim 14, wherein the method is performed by the first defibrillator, and
wherein causing the second therapy module to discharge the second defibrillation shock in accordance with the timing relationship comprises transmitting an instruction to the second defibrillator over a wired or a wireless connection.

20. The method of claim 14, wherein each of a first magnitude of the first defibrillation shock and a second magnitude of the second defibrillation shock is smaller than a combined magnitude of the first defibrillation shock and the second defibrillation shock occurring prior to a lagging edge of the second defibrillation shock and after a leading edge of the first defibrillation shock.

* * * * *